(12) United States Patent
Matsuhana et al.

(10) Patent No.: US 12,072,302 B2
(45) Date of Patent: Aug. 27, 2024

(54) X-RAY PHASE IMAGING SYSTEM

(71) Applicant: Shimadzu Corporation, Kyoto (JP)

(72) Inventors: Bunta Matsuhana, Kyoto (JP); Yuto Maeda, Kyoto (JP); Jiro Masuda, Kyoto (JP); Kana Kojima, Kyoto (JP); Takahiro Doki, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 185 days.

(21) Appl. No.: 17/977,011

(22) Filed: Oct. 31, 2022

(65) Prior Publication Data

US 2023/0194441 A1 Jun. 22, 2023

(30) Foreign Application Priority Data

Dec. 20, 2021 (JP) ................................. 2021-206399
May 23, 2022 (JP) ................................. 2022-083847

(51) Int. Cl.
*G01N 23/041* (2018.01)
*A61B 6/00* (2024.01)
*A61B 6/10* (2006.01)
*A61B 6/42* (2024.01)

(52) U.S. Cl.
CPC .......... *G01N 23/041* (2018.02); *A61B 6/102* (2013.01); *A61B 6/484* (2013.01); *A61B 6/4291* (2013.01)

(58) Field of Classification Search
CPC ............................. G01N 23/041; A61B 6/484
See application file for complete search history.

(56) References Cited

U.S. PATENT DOCUMENTS 5,812,629 A * 9/1998 Clauser .................. A61B 6/502
378/7
2019/0072501 A1 3/2019 Doki et al.
2023/0181136 A1* 6/2023 Kikuchi ................. A61B 6/483
382/128

FOREIGN PATENT DOCUMENTS

JP 201945412 A 3/2019

\* cited by examiner

*Primary Examiner* — Chih-Cheng Kao
(74) *Attorney, Agent, or Firm* — Maier & Maier, PLLC

(57) ABSTRACT

This X-ray phase imaging system includes a plurality of gratings including a first grating that is irradiated with X-rays from an X-ray source and a second grating that is irradiated with X-rays from the first grating. The X-ray phase imaging system includes an imaging unit that optically images a subject and one or both of the first grating and the second grating.

14 Claims, 6 Drawing Sheets

X-RAY PHASE IMAGING SYSTEM

CROSS-REFERENCE TO RELATED APPLICATIONS

The related application numbers JP2021-206399, X-ray Phase Imaging System, Dec. 20, 2021, Bunta Matsuhana, Yuto Maeda, Jiro Masuda, Kana Kojima, and Takahiro Doki, and JP2022-083847, X-ray Phase Imaging System, 2022 May 23, Bunta Matsuhana, Yuto Maeda, Jiro Masuda, Kana Kojima, and Takahiro Doki, upon which this patent application is based, are hereby incorporated by reference.

FIELD

The present invention relates to an X-ray phase imaging system.

BACKGROUND

Conventionally, an X-ray phase imaging apparatus is known. Such an apparatus is disclosed in, for example, JP-A-2019-45412.

The X-ray phase imaging apparatus disclosed in JP-A-2019-45412 uses the Talbot effect to image the inside of a subject and generate a phase contrast image. This X-ray phase imaging apparatus includes a first grating which is a phase grating that is used to form a self-image through the Talbot effect. The X-ray phase imaging apparatus disclosed in JP-A-2019-45412 moves a stage on which the subject is placed from a side of an X-ray source with respect to the first grating to a side of a detector with respect to the first grating beyond the first grating to change an enlargement/reduction ratio of the subject in the phase contrast image.

In the X-ray phase imaging apparatus, in either the case where the subject is disposed between the first grating and the X-ray source or the case where the subject is disposed between the first grating and the detector, a positional shift or an abnormality of the grating occurs in a case where the subject comes into contact with the grating during X-ray imaging or the like. In that case, it is not possible to generate an accurate phase contrast image. Although not particularly limited, there is a concern that, in a case where a CT image of the phase contrast image is acquired, the subject and the grating may come into contact with each other unexpectedly for a user because the subject placed on a placement stage is rotated. Although not particularly limited, there is a concern that, in a case where a fringe scanning method is used in the X-ray phase imaging apparatus, the subject and the grating may come into contact with each other unexpectedly for the user because the grating is moved in an in-plane direction perpendicular to an optical axis during X-ray imaging. Although not particularly limited, there is also a concern that, in a case where a plurality of phase contrast images are generated while the grating is rotated in the in-plane direction perpendicular to the optical axis during X-ray imaging in the X-ray phase imaging apparatus, the subject and the grating may come into contact with each other unexpectedly for the user. Therefore, in the X-ray phase imaging apparatus, there is a demand for a system capable of confirming whether or not the subject and the grating come into contact with each other by allowing the user to confirm a disposition relationship between the subject and the grating.

SUMMARY

The present invention has been made in order to solve the above-mentioned problems, and one object of the present invention is to provide an X-ray phase imaging system capable of confirming a disposition relationship between a subject and a grating.

An X-ray phase imaging system according to one aspect of the present invention comprises: an X-ray source that irradiates a subject with X-rays; a detector that detects the X-rays emitted from the X-ray source; a plurality of gratings that are disposed between the X-ray source and the detector, and that include a first grating which is irradiated with the X-rays from the X-ray source and a second grating which is irradiated with X-rays from the first grating; and an imaging unit that optically images the subject and one or both of the first grating and the second grating.

The imaging unit optically images the subject and the grating, whereby the disposition relationship between the subject and the grating can be confirmed. Therefore, it is possible to confirm whether or not the subject and the grating come into contact with each other. Further, although not particularly limited, it is necessary to change the position of the subject in the optical axis direction for enlargement/reduction, and it is necessary to rotate the subject in order to capture a CT image. Although not particularly limited, in the X-ray phase imaging system, the grating may be moved or rotated during X-ray imaging. Therefore, there is a concern that the subject and the grating may come into contact with each other unexpectedly for the user because the X-ray phase imaging system may include a grating that may be moved or rotated during imaging, as compared with a normal X-ray imaging apparatus. In consideration of this, in the present invention, the subject and the grating are optically imaged by the imaging unit, so that the user can confirm whether or not the subject and the grating come into contact with each other by viewing the captured image captured by the imaging unit.

DETAILED DESCRIPTION

Hereinafter, embodiments embodying the present invention will be described with reference to the drawings.

Configuration of X-Ray Phase Imaging System

The configuration of an X-ray phase imaging system 100 according to the present embodiment will be described with reference to FIGS. 1 to 6. The X-ray phase imaging system 100 is a system that images the inside of a subject 101 by using the phase difference of X-rays that have passed through the subject 101. In addition, the X-ray phase imaging system 100 is a system that images the inside of the subject 101 by using the Talbot effect. The X-ray phase imaging system 100 is used, for example, for non-destructive inspection applications to image the inside of the subject 101 as an object.

Configuration of Measurement System

Figure 1:
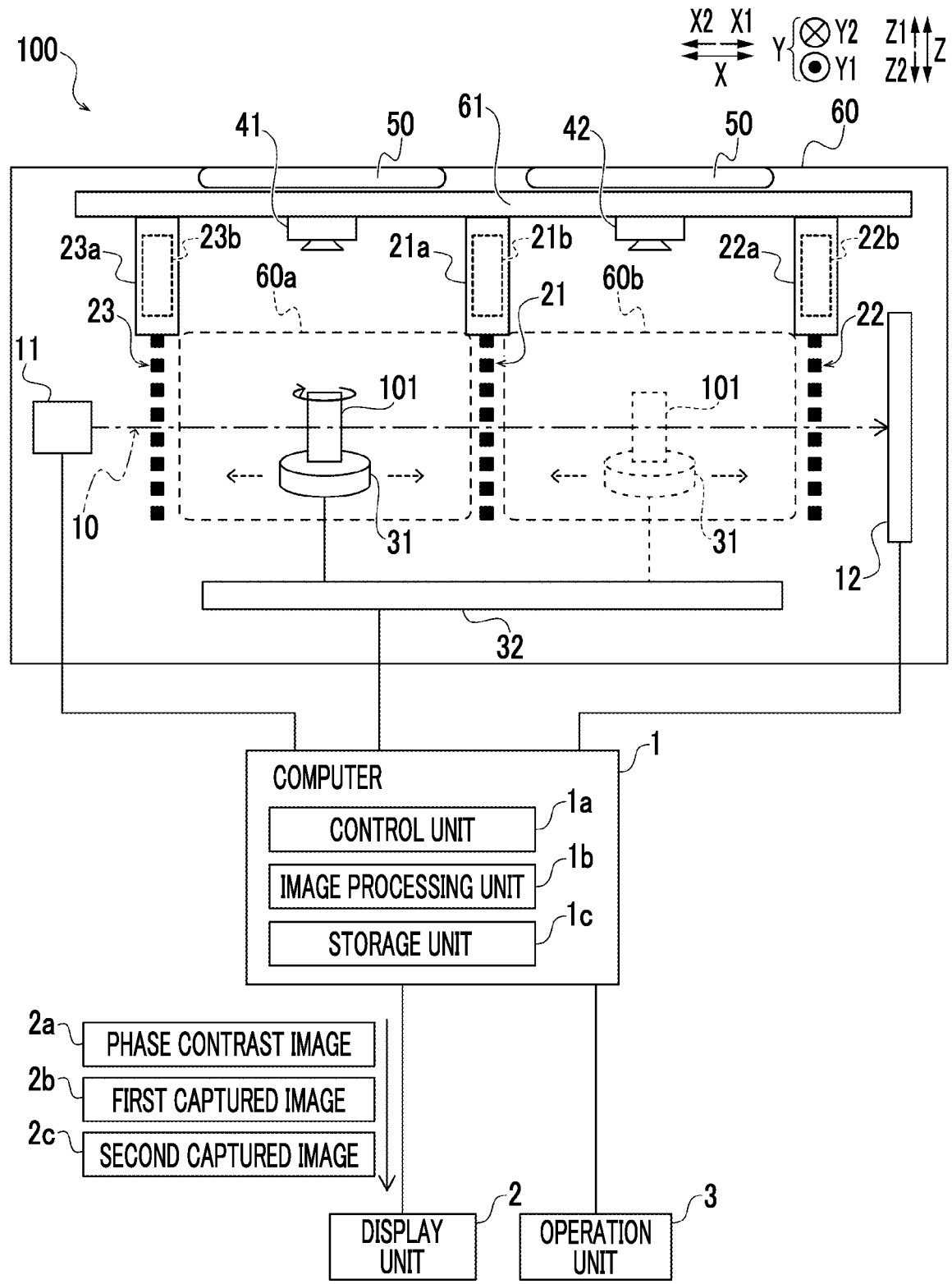
FIG. 1 is a schematic diagram showing a configuration of an X-ray phase imaging system.

As shown in FIG. 1, the X-ray phase imaging system 100 includes an X-ray source 11, a detector 12, and a plurality of gratings (a first grating 21, a second grating 22, and a third grating 23). The X-ray phase imaging system 100 is configured to generate a phase contrast image 2a by performing X-ray imaging using the plurality of gratings (the first grating 21, the second grating 22, and the third grating 23).

Specifically, in the X-ray phase imaging system 100, the X-ray source 11, the third grating 23, the first grating 21, the second grating 22, and the detector 12 are disposed side by side in this order along a direction (X direction) in which an X-ray irradiation axis 10 extends. That is, the first grating 21, the second grating 22, and the third grating 23 are disposed between the X-ray source 11 and the detector 12. In the present specification, an up-and-down direction is denoted by a Z direction, and the upper side (top surface side) is denoted by a Z1 direction, and the lower side (bottom surface side) is denoted by a Z2 direction. In addition, a direction from the X-ray source 11 to the detector 12 is denoted by an X direction, and one side (the side of the detector 12) is denoted by an X1 direction, and the other side (the side of the X-ray source 11) is denoted by an X2 direction. Further, a direction orthogonal to the Z direction and the X direction is denoted by a Y direction, and one side (front surface side) is denoted by a Y1 direction, and the other side (rear surface side) is denoted by a Y2 direction.

The X-ray source 11 is configured to irradiate the subject 101 with X-rays. Specifically, the X-ray source 11 includes an X-ray tube that generates X-rays when a high voltage is applied from a power supply unit (not shown), under the control performed by a control unit 1a, which will be described later.

The detector 12 is configured to detect the X-rays emitted from the X-ray source 11. Further, the detector 12 is configured to convert the detected X-ray into an electrical signal. The detector 12 is, for example, a flat panel detector (FPD). The detector 12 is composed of a plurality of conversion elements (not shown) and pixel electrodes (not shown) disposed on the plurality of conversion elements. The plurality of conversion elements and pixel electrodes are disposed side by side in the Y direction and the Z direction at a predetermined cycle (pixel pitch). Further, the detection signal (image signal) of the detector 12 is sent to an image processing unit 1b of a computer 1, which will be described later.

The first grating 21 has a so-called phase grating. The first grating 21 is disposed between the X-ray source 11 and the detector 12 and is irradiated with X-rays from the X-ray source 11. Specifically, the first grating 21 is disposed between the third grating 23 and the second grating 22 and is provided in order to form a self-image (through the Talbot effect) with the X-rays emitted from the X-ray source 11. The first grating 21 has slit portions and X-ray phase change portions arranged at a predetermined cycle (grating pitch) in the Z direction. The slit portions and X-ray phase change portions are each formed so as to extend linearly and parallel to each other in the Y direction. The Talbot effect means that when X-rays with coherence pass through the grating on which the slit portions are formed, a grating image (self-image) is formed at a position separated from the grating by a predetermined distance (Talbot distance).

The second grating 22 has a so-called absorption grating. The second grating 22 is irradiated with X-rays from the first grating 21. Specifically, the second grating 22 is disposed between the first grating 21 and the detector 12, and is configured to interfere with the self-image formed by the first grating 21. The second grating 22 has a plurality of X-ray transmission portions (slit portions) and a plurality of X-ray absorption portions arranged at a predetermined cycle (grating pitch) in the Z direction. The X-ray transmission portions and the X-ray absorption portions are each formed so as to extend linearly and parallel to each other in the Y direction. The second grating 22 is disposed at a position separated from the first grating 21 by a Talbot distance in order to cause the self-image and the second grating 22 to interfere with each other. The second grating 22 interferes with the self-image of the first grating 21 to form more fringes on the detection surface of the detector 12.

The third grating 23 has an absorption grating that enhances the coherence of X-rays emitted from the X-ray source 11. The third grating 23 is disposed between the X-ray source 11 and the first grating 21, and is irradiated with X-rays from the X-ray source 11. The third grating 23 has a plurality of slit portions and a plurality of X-ray absorption portions arranged at a predetermined cycle (pitch) in the Z direction. The slit portions and the X-ray absorption portions are each formed so as to extend linearly and parallel to each other in the Y direction. The third grating 23 is configured to make X-rays that have passed through each slit portion into a line light source corresponding to the position of each slit portion.

In the present specification, it is described that each of the first grating 21, the second grating 22, and the third grating 23 includes not only the grating but also a cover member covering the grating.

Configuration of Housing

Further, as shown in FIG. 1, the X-ray phase imaging system 100 includes a housing 60. The housing 60 houses the X-ray source 11, the detector 12, and the plurality of gratings (the first grating 21, the second grating 22, and the third grating 23) therein. In addition, the housing 60 houses a placement stage 31, a drive unit 32, a first imaging unit 41, a second imaging unit 42, and an illumination unit 50, which will be described later, therein. The drive unit 32 is an example of the "placement stage drive unit" in the scope of the claims.

The housing 60 has a substantially rectangular parallelepiped shape, and the inside is hollow. Further, the housing 60 has a door portion (not shown) that is provided on the surface of the housing 60 on the front surface side (Y1 direction side) and that is used to access the inside. The housing 60 has a structure that restrains X-rays from leaking to the outside of the housing 60 in a state in which the door portion provided on the front surface side is closed. For example, the housing 60 has a wall surface formed of a metal such as lead that shields X-rays so as to restrain X-rays emitted from the X-ray source 11 from leaking to the outside. The door portion that is used to access the inside of the housing 60 is not opened while X-ray imaging is being performed (while X-rays are being emitted from the X-ray source 11) and while the placement stage 31, which will be described later, is being moved.

Further, a first region 60a in which the subject 101 is disposed and a second region 60b different from the first region 60a are provided inside the housing 60. The first region 60a is a region provided on the side of the X-ray source 11 (X2 direction side) with respect to the first grating 21. Specifically, the first region 60a is a region provided between the first grating 21 and the third grating 23. Further, the second region 60*b* is a region provided on the side of the detector 12 (X1 direction side) with respect to the first grating 21. Specifically, the second region 60*b* is a region provided between the first grating 21 and the second grating 22. The enlargement ratios of the acquired phase contrast images 2*a* are different from each other between the first region 60*a* and the second region 60*b*. In a case where it is desired to observe a minute region of the subject 101 with a large enlargement ratio, the subject 101 is disposed in the first region 60*a*. Further, in a case where it is desired to observe a wide region of the subject 101 with a small enlargement ratio, the subject 101 is disposed in the second region 60*b*.

The housing 60 has a frame member 61 therein. The frame member 61 is a member having a rod shape (beam shape) provided inside the housing 60 on the upper top surface side (Z1 direction side) so as to extend in the X direction. A grating holding unit 21*a*, a grating holding unit 22*a*, and a grating holding unit 23*a* that hold the plurality of gratings (the first grating 21, the second grating 22, and the third grating 23) from above are disposed on the frame member 61. Specifically, the grating holding unit 21*a*, the grating holding unit 22*a*, and the grating holding unit 23*a* hold the first grating 21, the second grating 22, and the third grating 23 such that the first grating 21, the second grating 22, and the third grating 23 are suspended from above, respectively. Further, the grating holding units 21*a*, 22*a*, and 23*a* have a grating drive unit 21*b*, a grating drive unit 22*b*, and a grating drive unit 23*b*, such as an actuator, respectively, and the grating drive unit 21*b*, the grating drive unit 22*b*, and the grating drive unit 23*b* are configured to change the positions and the angles of the first grating 21, the second grating 22, and the third grating 23, respectively. Specifically, the grating drive unit 21*b*, the grating drive unit 22*b*, and the grating drive unit 23*b* move the first grating 21, the second grating 22, and the third grating 23 and rotate the first grating 21, the second grating 22, and the third grating 23, respectively. For example, in a case where the fringe scanning method is used to generate the phase contrast image 2*a*, it is necessary to move the second grating 22 relative to the first grating 21 in the Z direction by using the drive mechanism (grating drive units 21*b*, 22*b*, and 23*b*). For example, in a case where carbon fibers inside carbon fiber reinforced plastics (CFRP) are imaged, the first grating 21, the second grating 22, and the third grating 23 are rotated at a plurality of angles in the in-plane direction orthogonal to the X-ray irradiation axis 10 (X direction) by the grating drive units 21*b*, 22*b*, and 23*b*, respectively, and the phase contrast image 2*a* at each angle is generated.

Configuration of Drive System

Figure 2:
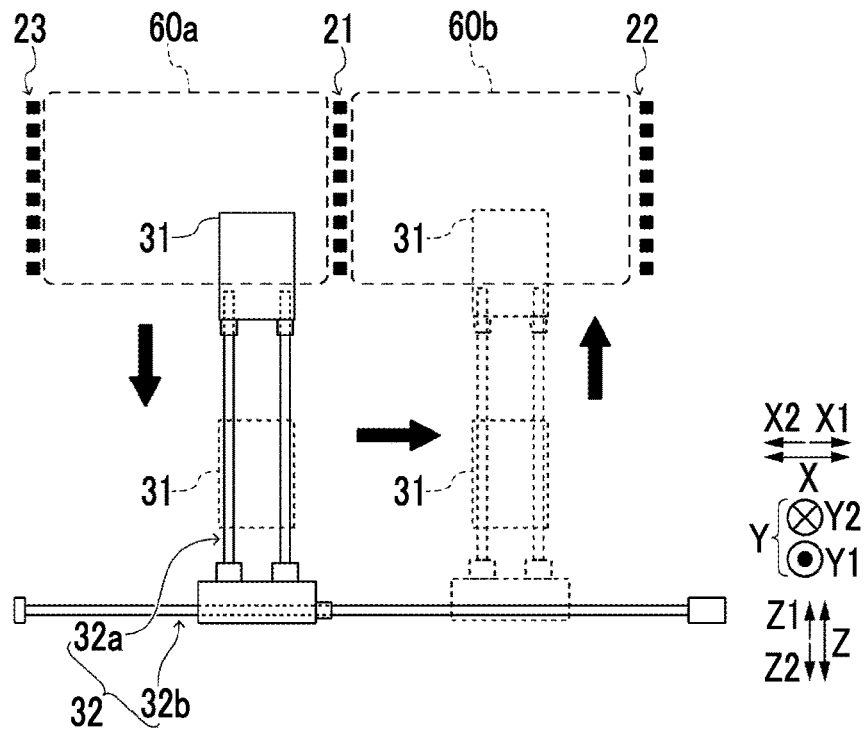
FIG. 2 is a view illustrating movement of a placement stage beyond a first grating.
Figure 3:
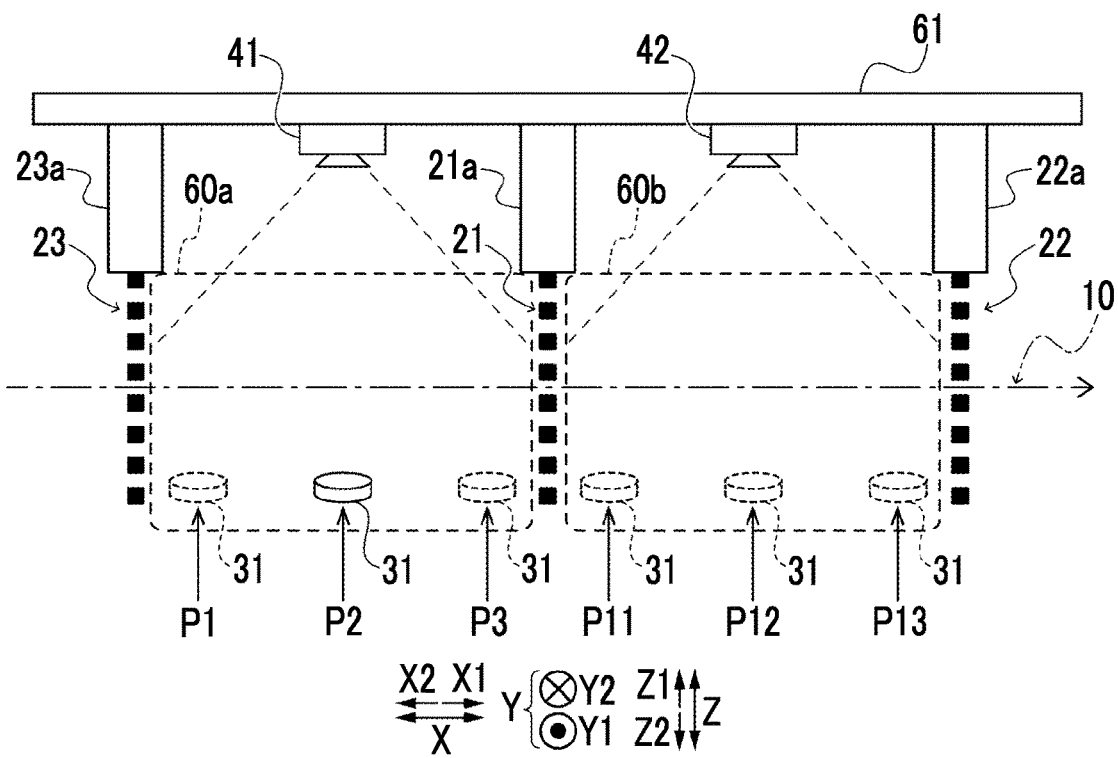
FIG. 3 is a view illustrating disposition between the placement stage and a first and second imaging units.

As shown in FIGS. 1 to 3, the X-ray phase imaging system 100 includes the placement stage 31 and the drive unit 32. The X-ray phase imaging system 100 is configured to change the disposition of the subject 101 by moving the placement stage 31.

As shown in FIG. 1, in the present embodiment, the subject 101 is placed on the placement stage 31. Further, the placement stage 31 is configured to rotate the subject 101 with the Z direction (up-and-down direction) as the rotation axis in a state in which the subject 101 is placed thereon. The X-ray phase imaging system 100 is configured to rotate the subject 101 placed on the placement stage 31 by rotating only the placement stage 31 itself or a rotary shaft. Then, in the X-ray phase imaging system 100, X-ray imaging is performed while the subject 101 is rotated with the Z direction as the rotation axis. Further, the placement stage 31 is configured to change the disposition position in the X direction.

Specifically, as shown in FIG. 2, the placement stage 31 is configured to move in the X direction beyond the first grating 21 between the side of the X-ray source 11 of the first grating 21 and the side of the detector 12 of the first grating 21 by the drive performed by the drive unit 32. That is, in the present embodiment, the placement stage 31 is configured to move between the first region 60*a* provided on the side of the X-ray source 11 (X2 direction side) with respect to the first grating 21 and the second region 60*b* provided on the side of the detector 12 (X1 direction side) with respect to the first grating 21. In other words, in the present embodiment, the placement stage 31 is selectively disposed in the first region 60*a* or the second region 60*b*. It is preferable that the movement of the placement stage 31 beyond the first grating 21 is performed in a state in which the subject 101 is not placed thereon.

The drive unit 32 has a first drive mechanism 32*a* and a second drive mechanism 32*b*. The first drive mechanism 32*a* includes, for example, a ball screw member and a motor, and moves the placement stage 31 up and down along the Z direction. Further, the second drive mechanism 32*b* also includes a ball screw member and a motor, and is configured to move the placement stage 31 along the X direction. Specifically, in a case where the placement stage 31 moves beyond the first grating 21, the placement stage 31 is configured to move in the X direction beyond the first grating 21 by retracting toward the Z2 direction side by the first drive mechanism 32*a* of the drive unit 32 and then by passing below (Z2 direction side) the first grating 21 by the second drive mechanism 32*b* of the drive unit 32. The drive unit 32 moves the placement stage 31 on the basis of a control signal from the control unit 1*a* of the computer 1, which will be described later. Further, the drive unit 32 includes an encoder (not shown) that acquires the rotation speed (rotation angle) of the motor, and is configured to transmit position information indicating the position of the placement stage 31 to the control unit 1*a*. Specifically, the drive unit 32 transmits a pulse signal indicating the rotation speed of the motor acquired by the encoder to the control unit 1*a* as the position information.

Further, as shown in FIG. 3, the placement stage 31 is configured to move to six positions, that is, a position P1, a position P2, and a position P3 provided on the side of the X-ray source 11 (first region 60*a*) with respect to the first grating 21 and a position P11, a position P12, and a position P13 provided on the side of the detector 12 (second region 60*b*) with respect to the first grating 21, on the basis of the input operation with respect to an operation unit 3, which will be described later. The position P2 is an intermediate position in the X direction between the first grating 21 and the third grating 23, in the first region 60*a*. The position P1 is a position on the side of the third grating 23 (X2 direction side) with respect to the position P2 in the first region 60*a*. Further, the position P3 is a position on the side of the first grating 21 (X1 direction side) with respect to the position P2 in the first region 60*a*. The position P12 is an intermediate position in the X direction between the first grating 21 and the second grating 22, in the second region 60*b*. The position P11 is a position on the side of the first grating 21 (X2 direction side) with respect to the position P12 in the second region 60*b*. Further, the position P13 is a position on the side of the second grating 22 (X1 direction side) with respect to the position P12 in the second region 60*b*.

Further, the placement stage 31 is configured to finely adjust the disposition position along the X direction from a state in which the positions P1 to P3 and the positions P11 to P13 are disposed, on the basis of the input operation with respect to the operation unit 3.

Configuration for Capturing Image of External Appearance

As shown in FIG. 1, the X-ray phase imaging system 100 includes the imaging unit that optically images the subject 101 and the grating (the first grating 21, the second grating 22, and the third grating 23). In the present embodiment, the imaging unit includes the first imaging unit 41 and the second imaging unit 42 provided separately from the first imaging unit 41. The term "optical imaging" as used herein means imaging the external appearance of the subject 101, not the X-ray imaging of imaging the inside of the subject 101. The X-ray phase imaging system 100 is configured to image the external appearance of the subject 101 disposed inside the housing 60. The first imaging unit 41 is an example of the "imaging unit" and the "first imaging unit" in the scope of the claims. The second imaging unit 42 is an example of the "imaging unit" and the "second imaging unit" in the scope of the claims.

The first imaging unit 41 and the second imaging unit 42 have, for example, a charge-coupled device image sensor (CCD image sensor) as a plurality of imaging elements, and optically image the external appearance of the subject 101 placed on the placement stage 31. Further, the first imaging unit 41 and the second imaging unit 42 output images (a first captured image 2b and a second captured image 2c) captured as detection signals by the imaging elements to the image processing unit 1b of the computer 1, which will be described later. The first captured image 2b is an example of the "captured image" and the "first captured image" in the scope of the claims. Further, the second captured image 2c is an example of the "captured image" and the "second captured image" in the scope of the claims.

Figure 4:
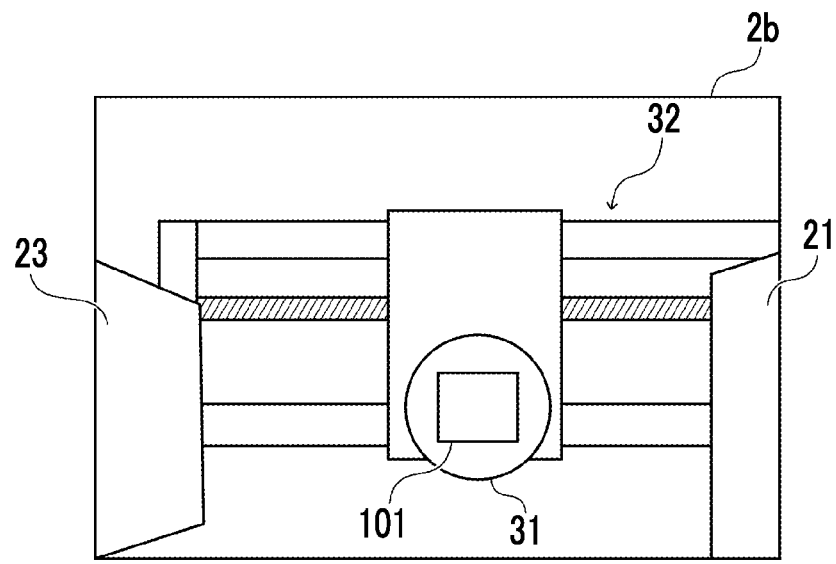
FIG. 4 is a view showing a first captured image captured by the first imaging unit.

As shown in FIG. 4, in the present embodiment, the first captured image 2b is captured by the first imaging unit 41. Specifically, the first imaging unit 41 is configured to image the subject 101 disposed in the first region 60a and the first grating 21 and the third grating 23 which are gratings adjacent to the first region 60a. That is, the first imaging unit 41 has an angle of view capable of imaging both the first grating 21 and the third grating 23 so that the entire first region 60a is imaged.

Figure 5:
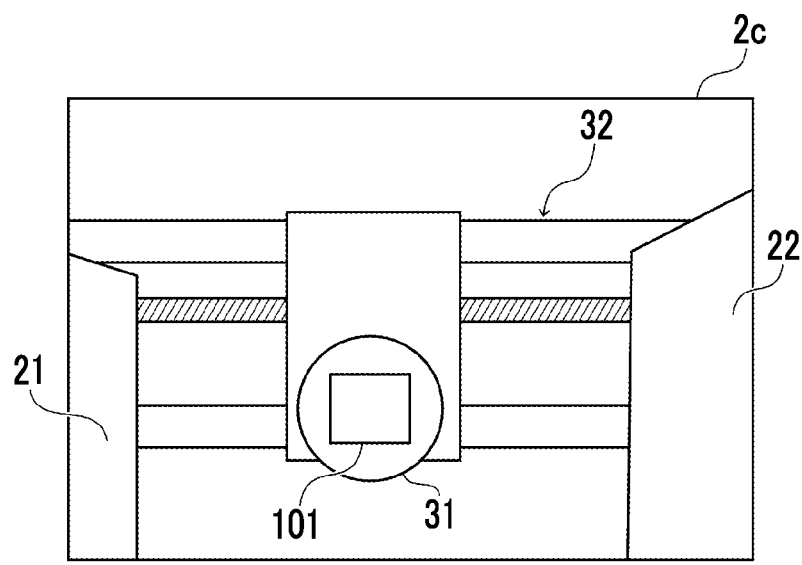
FIG. 5 is a view showing a second captured image captured by the second imaging unit.

Further, as shown in FIG. 5, in the present embodiment, the second captured image 2c is captured by the second imaging unit 42. Specifically, the second imaging unit 42 is configured to image the subject 101 disposed in the second region 60b and the first grating 21 and the second grating 22 which are gratings adjacent to the second region 60b. That is, the second imaging unit 42 has an angle of view capable of imaging both the first grating 21 and the second grating 22 so that the entire second region 60b is imaged.

Further, as shown in FIG. 3, in the present embodiment, the first imaging unit 41 is disposed at a position separated from the position where the subject 101 is disposed in a direction (Z direction) perpendicular to the X-ray irradiation axis 10 (X direction) from the X-ray source 11 to the detector 12, in the first region 60a. Similarly, the second imaging unit 42 is disposed at a position separated from the position where the subject 101 is disposed in the direction perpendicular to the X-ray irradiation axis 10 (Z direction), in the second region 60b. Here, the X-ray irradiation axis 10 is an axis from the X-ray source 11 to the detector 12. Specifically, the X-ray irradiation axis 10 is the central axis of X-rays emitted from the X-ray source 11, and is an axis that extends along the X-ray irradiation direction (X direction) and that is perpendicular to the detection surface of the detector 12.

For example, the first imaging unit 41 and the second imaging unit 42 are disposed inside the housing 60 on the upper side (top surface side, Z1 direction side) in the vertical direction (Z direction). Specifically, the first imaging unit 41 is disposed above the first region 60a. Further, the second imaging unit 42 is disposed above the second region 60b. The first imaging unit 41 and the second imaging unit 42 are disposed by being screwed to the frame member 61 provided on the upper side of the housing 60 by a fastening member such as a screw. That is, the first imaging unit 41 and the second imaging unit 42 are configured to image the subject 101 placed on the placement stage 31 from a common direction. The first imaging unit 41 and the second imaging unit 42 are disposed so as to image the subject 101 and the plurality of gratings from the direction side on which the grating holding units 21a, 22a, and 23a that hold the plurality of gratings are disposed.

Specifically, the first imaging unit 41 is disposed at a position perpendicularly separated in the Z direction from the intermediate position in the X direction between the first grating 21 and the third grating 23, with respect to the X-ray irradiation axis 10 (X direction). Then, the first imaging unit 41 performs imaging downward (Z2 direction) in a direction perpendicular to the X-ray irradiation axis 10. That is, the first imaging unit 41 is disposed directly above the position P2. Therefore, the first imaging unit 41 is disposed on the rotation axis of the placement stage 31 (subject 101) that rotates at the position P2 of the first region 60a. In other words, the first imaging unit 41 is disposed at a position separated in the direction along the rotation axis of the placement stage 31 (subject 101) while the placement stage 31 is disposed in the first region 60a.

Similarly, the second imaging unit 42 is disposed at a position perpendicularly separated in the Z direction from the intermediate position in the X direction between the first grating 21 and the second grating 22, with respect to the X-ray irradiation axis 10 (X direction) from the X-ray source 11 to the detector 12. Then, the second imaging unit 42 performs imaging downward (Z2 direction) in a direction perpendicular to the X-ray irradiation axis 10. That is, the second imaging unit 42 is disposed directly above the position P12. Therefore, the second imaging unit 42 is disposed on the rotation axis of the placement stage 31 (subject 101) that rotates at the position P12 of the second region 60b. In other words, the second imaging unit 42 is disposed at a position separated in the direction along the rotation axis of the placement stage 31 (subject 101) while the placement stage 31 is disposed in the second region 60b.

In addition, as shown in FIG. 1, in the present embodiment, the X-ray phase imaging system 100 includes the illumination unit 50. The illumination unit 50 irradiates the subject 101 with illumination light. The illumination unit 50 has, for example, a light emitting diode (LED) that emits white light. The illumination unit 50 is disposed inside the housing 60 on the top surface (the surface on the Z1 direction side). For example, two illumination units 50 are provided so as to correspond to the first imaging unit 41 and the second imaging unit 42, respectively. Further, the illumination unit 50 starts emitting illumination light when the power of the X-ray phase imaging system 100 is turned on. The illumination unit 50 is configured to continuously emit illumination light not only before X-ray irradiation is started from the X-ray source 11, but also while the X-ray irradiation is being performed from the X-ray source 11 (while X-ray imaging is being performed). That is, the illumination unit 50 is configured to continuously emit illumination light regardless of the opening and closing of the door portion (not shown) of the housing 60. In the present embodiment, the first imaging unit 41 and the second imaging unit 42 are configured to image the subject 101 while the subject 101 is irradiated with illumination light from the illumination unit 50.

Configuration for Generation and Display of Image

As shown in FIG. 1, the X-ray phase imaging system 100 of the present embodiment includes the computer 1, a display unit 2, and the operation unit 3. For example, the computer 1, the display unit 2, and the operation unit 3 are disposed outside (on the outer surface of) the housing 60. The display unit 2 is an example of the "display device" in the scope of the claims.

The computer 1 includes the control unit 1a, the image processing unit 1b, and a storage unit 1c. Then, the computer 1 is configured to generate a phase contrast image 2a by performing X-ray imaging using the plurality of gratings (the first grating 21, the second grating 22, and the third grating 23). Further, the computer 1 generates the first captured image 2b captured by the first imaging unit 41 and the second captured image 2c captured by the second imaging unit 42. The control unit 1a is an example of the "display control unit" in the scope of the claims.

The control unit 1a controls each unit of the X-ray phase imaging system 100. Specifically, the control unit 1a is configured to control the operation of the drive unit 32. Further, the control unit 1a controls the X-ray irradiation performed by the X-ray source 11. Further, the control unit 1a causes the display unit 2 to display the image generated by the image processing unit 1b. The control unit 1a includes, for example, a central processing unit (CPU), a read only memory (ROM), and a (random access memory (RAM).

The image processing unit 1b is configured to generate the phase contrast image 2a on the basis of the detection signal sent from the detector 12. The image processing unit 1b includes, for example, a processor such as a graphics processing unit (GPU) or a field-programmable gate array (FPGA) configured for image processing. The phase contrast image 2a is a general term for images obtained by using the plurality of gratings (the first grating 21, the second grating 22, and the third grating 23), and includes, for example, at least one of an absorption image, a phase differential image, and a dark field image. The absorption image is an X-ray image imaged on the basis of the difference in the degree of X-ray absorption of the subject 101. The phase differential image is an X-ray image imaged on the basis of the phase shift of X-rays. The dark field image is a visibility image obtained by a change in visibility based on the small-angle scattering of the object. The dark field image is also called a small-angle scattering image. "Visibility" is sharpness.

Further, the image processing unit 1b is configured to generate the first captured image 2b and the second captured image 2c. Specifically, the image processing unit 1b generates the first captured image 2b captured by the first imaging unit 41 on the basis of the detection signal from the first imaging unit 41. Further, the image processing unit 1b generates the second captured image 2c captured by the second imaging unit 42 on the basis of the detection signal from the second imaging unit 42.

The storage unit 1c is configured to store the phase contrast image 2a generated by the image processing unit 1b and various programs executed by the control unit 1a. The storage unit 1c includes a non-volatile memory such as a hard disk drive (HDD) or a solid state drive (SSD).

In the X-ray phase imaging system 100, X-ray imaging is performed a plurality of number of times while rotating the subject 101 placed on the placement stage 31 by rotating the placement stage 31. The image processing unit 1b is configured to generate a plurality of phase contrast images 2a by performing X-ray imaging a plurality of number of times, and to generate a three-dimensional phase contrast image 2a (CT image) on the basis of the plurality of phase contrast images 2a.

The display unit 2 includes, for example, a liquid crystal monitor. The display unit 2 displays the image under the control performed by the control unit 1a. Specifically, the display unit 2 displays the phase contrast image 2a generated by the image processing unit 1b. Further, the display unit 2 is configured to selectively display the first captured image 2b captured by the first imaging unit 41 and the second captured image 2c captured by the second imaging unit 42. Details of the display control for the display unit 2 will be described later.

The operation unit 3 is configured to receive the operation input of an operator. The operation unit 3 includes, for example, an input device, such as a keyboard and a mouse. In the present embodiment, the operation unit 3 receives an input operation to move the placement stage 31. Further, the operation unit 3 receives an input operation to start X-ray imaging for generating the phase contrast image 2a.

Details of Control of X-ray Phase Imaging System

In the present embodiment, the control unit 1a is configured to change the position of the placement stage 31 on the basis of the input operation with respect to the operation unit 3. Further, the control unit 1a is configured to cause the display unit 2 to selectively display the first captured image 2b captured by the first imaging unit 41 or the second captured image 2c captured by the second imaging unit 42.

Figure 6:
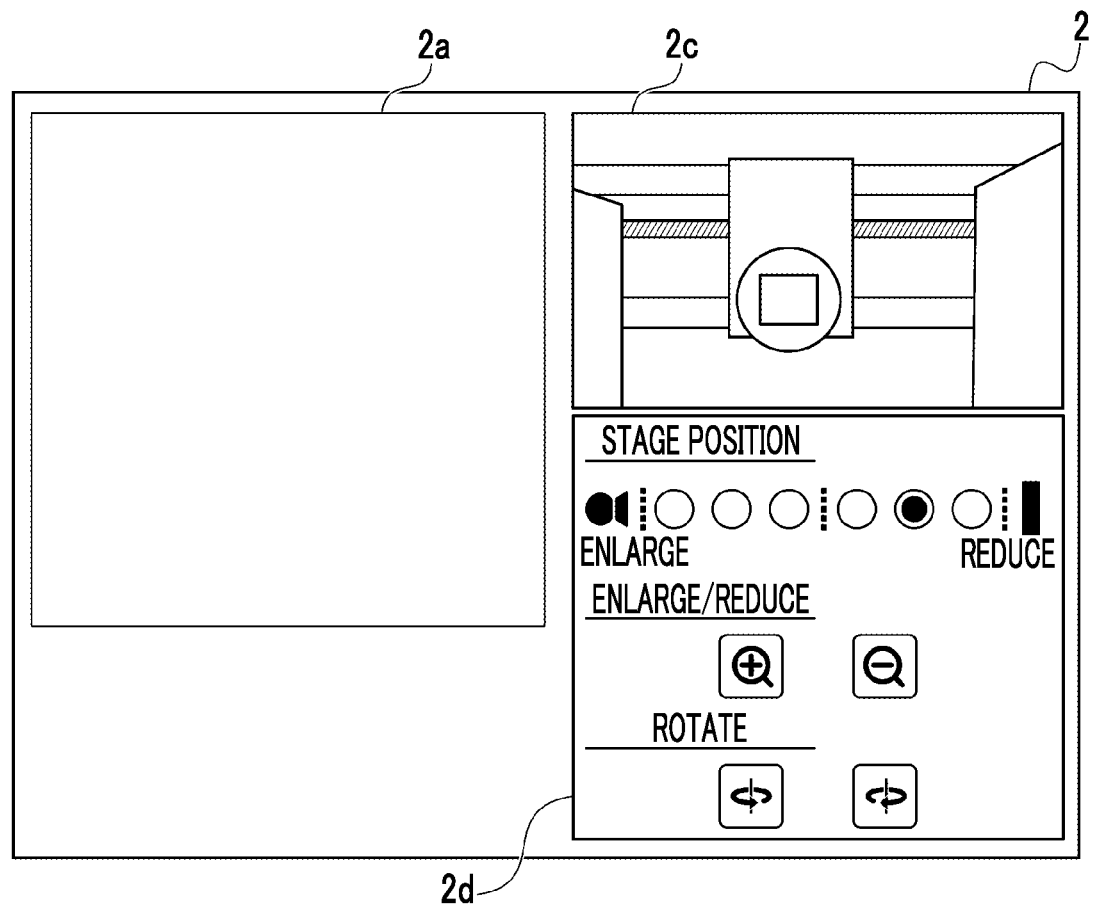
FIG. 6 is a view showing an example of display of a display unit.

Specifically, as shown in FIG. 6, the control unit 1a causes the display unit 2 to display the phase contrast image 2a and one of the first captured image 2b and the second captured image 2c side by side. Further, in a case where the placement stage 31 is disposed in the first region 60a, the control unit 1a causes the display unit 2 to display the first captured image 2b. Then, in a case where the placement stage 31 is disposed in the second region 60b, the control unit 1a causes the display unit 2 to display the second captured image 2c. The position of the placement stage 31 is acquired on the basis of the position information transmitted from the drive unit 32. Further, the first captured image 2b and the second captured image 2c are displayed on the display unit 2 as moving images. FIG. 6 shows an example in which the placement stage 31 is disposed at the position P12 of the second region 60b, and the second captured image 2c is displayed on the display unit 2. Further, FIG. 6 shows a state before the start of X-ray irradiation from the X-ray source 11. Therefore, nothing is displayed in the phase contrast image 2a.

Further, the control unit 1a displays display indicating the current disposition position of the placement stage 31 as a "stage position" in a region 2d of the display unit 2. Then, the operation unit 3 receives an input operation for changing the positions (the positions P1 to P3 and the positions P11 to P13) of the placement stage 31 through an operation such as a click operation with respect to the region 2d. Then, the control unit 1a is configured to move the placement stage 31 to a selected position on the basis of the received input operation. The control unit 1a is configured not to receive the input operation to move the placement stage 31 such that the operator does not come into contact with the placement stage 31 in motion, in a case where the door portion of the housing 60 is in the opened state.

Here, in the present embodiment, the control unit 1*a* is configured to switch between the display of the first captured image 2*b* on the display unit 2 and the display of the second captured image 2*c* on the display unit 2, on the basis of the movement of the placement stage 31 performed by the drive unit 32. The control unit 1*a* is configured to acquire the position of the placement stage 31 and to switch between the displays on the display unit 2, on the basis of the position information of the placement stage 31 transmitted from the drive unit 32. Specifically, the control unit 1*a* acquires a pulse signal indicating the rotation speed of the motor acquired by the encoder provided in the drive unit 32, as the position information. Then, the control unit 1*a* calculates the drive position (disposition position) of the placement stage 31 from the number of pulses (rotation speed of the motor) of the acquired pulse signal. Further, the control unit 1*a* determines whether the placement stage 31 is disposed in the first region 60*a* or the second region 60*b*, on the basis of the correspondence relationship between the first region 60*a* or the second region 60*b* and the drive position set in advance. For example, in a case where the placement stage 31 moves from the first region 60*a* to the second region 60*b* on the basis of the movement of the placement stage 31 performed by the drive unit 32, the control unit 1*a* is configured to switch the display from the first captured image 2*b* to the second captured image 2*c* to cause the display unit 2 to display the second captured image 2*c*. The first captured image 2*b* and the second captured image 2*c* are displayed in the same region of the display unit 2 by being switched therebetween.

Further, in the present embodiment, the first imaging unit 41 is configured to image the subject 101 (placement stage 31) in motion that is moving in the first region 60*a* on the basis of the input operation with respect to the operation unit 3. Then, the second imaging unit 42 is configured to image the subject 101 (placement stage 31) in motion that is moving in the second region 60*b* on the basis of the input operation with respect to the operation unit 3. The control unit 1*a* is configured to cause the display unit 2 to display the first captured image 2*b* or the second captured image 2*c* as a moving image obtained by imaging the subject 101 (placement stage 31) in motion.

For example, the control unit 1*a* executes an operation to finely adjust the enlargement/reduction of the subject 101 in the phase contrast image 2*a* by finely adjusting the position of the placement stage 31 on the basis of the input operation with respect to the region 2*d* of the display unit 2. Specifically, the operation unit 3 receives an operation to finely adjust the position of the subject 101 (the position of the placement stage 31) from the operator, before the start of X-ray imaging for generating the phase contrast image 2*a*. Then, the control unit 1*a* controls the drive unit 32 to finely adjust the position of the placement stage 31 on the basis of the received operation. In a case where the operation for enlarging the subject 101 of the phase contrast image 2*a* is received, the control unit 1*a* moves the placement stage 31 from the current disposition position to the side of the X-ray source 11 (X2 direction side). In a case where the operation for reducing the subject 101 of the phase contrast image 2*a* is received, the control unit 1*a* moves the placement stage 31 from the current disposition position to the side of the detector 12 (X1 direction side). Then, the control unit 1*a* causes the display unit 2 to display the first captured image 2*b* or the second captured image 2*c* obtained by imaging the subject 101 in motion so that the movement state of the subject 101 placed on the placement stage 31 can be confirmed.

Further, the control unit 1*a* executes an operation to rotate the placement stage 31 on the basis of the input operation with respect to the region 2*d* of the display unit 2. For example, the operator's operation to rotate the placement stage 31 on which the subject 101 is placed is received by the operation unit 3 before the start of X-ray imaging The control unit 1*a* rotates the placement stage 31 on the basis of the received operation. The first imaging unit 41 images the subject 101 placed on the placement stage 31 rotating in the first region 60*a*. Similarly, the second imaging unit 42 images the subject 101 placed on the placement stage 31 rotating in the second region 60*b*. Then, the control unit 1*a* causes the display unit 2 to display the first captured image 2*b* or the second captured image 2*c* obtained by imaging the rotating subject 101 so that the state of the rotating subject 101 can be confirmed.

Then, the control unit 1*a* starts X-ray imaging for generating the phase contrast image 2*a*, on the basis of the input operation with respect to the operation unit 3. Specifically, the control unit 1*a* causes the X-ray source 11 to start X-ray irradiation, on the basis of the input operation with respect to the operation unit 3. Then, the control unit 1*a* causes the display unit 2 to display the phase contrast image 2*a* generated by the image processing unit 1*b*.

The first imaging unit 41 images the subject 101 that rotates in the first region 60*a*, and the second imaging unit 42 images the subject 101 that rotates in the second region 60*b*, during X-ray imaging. Further, during X-ray imaging, the first imaging unit 41 images the first grating 21 and the third grating 23 that are moving or rotating, or are stopped, and the second imaging unit 42 images the first grating 21 and the second grating 22 that are moving or rotating, or are stopped. The control unit 1*a* is configured to cause the display unit 2 to display the first captured image 2*b* or the second captured image 2*c* while X-ray imaging is being performed (while X-rays from the X-ray source 11 are being emitted). Further, the control unit 1*a* causes the display unit 2 to display the first captured image 2*b* or the second captured image 2*c* with a reduced frame rate in order to reduce the processing load, during X-ray imaging. The control unit 1*a* is configured to cause the display unit 2 to continuously display the first captured image 2*b* or the second captured image 2*c* even in a case where the X-ray imaging is finished. Therefore, the X-ray phase imaging system 100 of the present embodiment is configured to confirm the disposition of the subject 101 and the gratings inside the housing 60 by allowing the operator to confirm the first captured image 2*b* or the second captured image 2*c* even in a case where the X-ray imaging is finished and the display of the phase contrast image 2*a* is finished.

The control unit 1*a* is configured to cause the display unit 2 to display the first captured image 2*b* or the second captured image 2*c* even in a case where the subject 101 is not placed on the placement stage 31.

Figure 7:
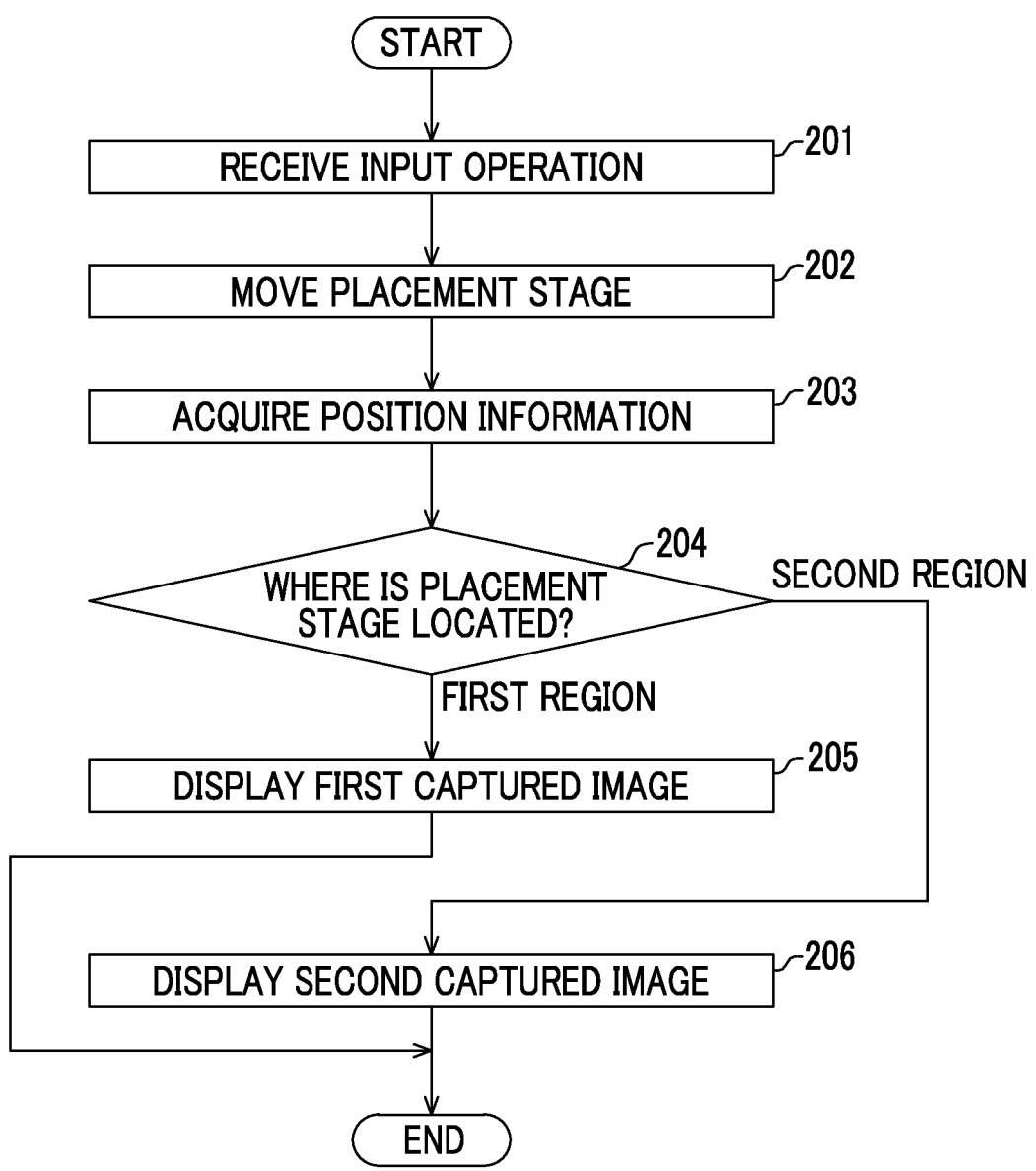
FIG. 7 is a flowchart illustrating switch of the display of the display unit.

Control Processing Flow of Switching Display Between First Captured Image and Second Captured Image Next, with reference to FIG. 7, a control processing flow of switching between the display of the first captured image 2*b* and the display of the second captured image 2*c* performed by the X-ray phase imaging system 100 of the present embodiment will be described.

First, in step 201, an input operation for moving the placement stage 31 is received. That is, the input operation is received in order to change the position of the placement stage 31 on the basis of the input operation with respect to the operation unit 3.

Next, in step 202, the placement stage 31 is moved on the basis of the input operation received by the operation unit 3. Specifically, the operation of the drive unit 32 is controlled on the basis of the input operation received by the operation unit 3, whereby the placement stage 31 is moved.

Next, in step 203, the position information of the placement stage 31 is acquired. Specifically, the pulse signal from the encoder provided in the drive unit 32 is acquired as the position information of the placement stage 31. That is, the position information is acquired as a feedback signal transmitted from the drive unit 32.

Next, in step 204, whether the placement stage 31 is disposed in the first region 60a or the second region 60b is determined on the basis of the acquired position information. In a case where determination is made that the placement stage 31 is disposed in the first region 60a, the process proceeds to step 205. In a case where determination is made that the placement stage 31 is disposed in the second region 60b, the process proceeds to step 206.

In step 205, since determination is made that the placement stage 31 is disposed in the first region 60a, the first captured image 2b is displayed on the display unit 2. That is, while the placement stage 31 is disposed in the second region 60b and the second captured image 2c is displayed on the display unit 2, the display is switched from the second captured image 2c and the first captured image 2b is displayed on the display unit 2.

Further, in step 206, since determination is made that the placement stage 31 is disposed in the second region 60b, the second captured image 2c is displayed on the display unit 2. That is, while the placement stage 31 is disposed in the first region 60a and the first captured image 2b is displayed on the display unit 2, the display is switched from the first captured image 2b, and the second captured image 2c is displayed on the display unit 2.

The acquisition of the position information in steps 203 to 206 and the control processing of the display of the first captured image 2b or the second captured image 2c may be sequentially repeatedly executed for each predetermined interval in a period in which the placement stage 31 is moved in step 202, or may be executed after the movement of the placement stage 31 in step 202 is completed. Further, prior to step 201 and the movement of the placement stage 31 in step 202, the first captured image 2b and the second captured image 2c are displayed on the display unit 2 on the basis of the acquired position information.

Effect of Present Embodiment

In the present embodiment, the following effects can be obtained.

In the present embodiment, the X-ray phase imaging system 100 includes the imaging unit (the first imaging unit 41 and the second imaging unit 42) that optically images the subject 101 and the grating (the first grating 21, the second grating 22, and the third grating 23), whereby the disposition relationship between the subject 101 and the grating can be confirmed. Therefore, it is possible to confirm that the subject 101 and the grating do not come into contact with each other. Here, it is necessary to change the position of the subject 101 in the optical axis direction (direction along the X-ray irradiation axis 10) for enlargement/reduction, and it is necessary to rotate the subject 101 in order to capture a CT image. Then, in the X-ray phase imaging system 100, the grating (the first grating 21, the second grating 22, and the third grating 23) may be moved or rotated during X-ray imaging Therefore, there is a concern that the subject 101 and the grating (the first grating 21, the second grating 22, and the third grating 23) may come into contact with each other unexpectedly for the user (operator) because the X-ray phase imaging system 100 may include a grating that may be moved or rotated during imaging as compared with a normal X-ray imaging apparatus. In consideration of this, in the present embodiment, the subject 101 and the grating are optically imaged by the first imaging unit 41 and the second imaging unit 42, so that the operator can confirm whether or not the subject 101 and the grating come into contact with each other by viewing the captured image (the first captured image 2b and the second captured image 2c) captured by the imaging unit (the first imaging unit 41 and the second imaging unit 42).

Further, in the present embodiment, further effects can be obtained by adopting the following configuration.

That is, the first imaging unit 41 and the second imaging unit 42 (imaging unit) optically image the subject 101 and the grating (the first grating 21 and the third grating 23) adjacent to the first region 60a among the plurality of gratings in a case where the subject 101 is disposed in the first region 60a on the side of the X-ray source 11 with respect to the first grating 21, and optically image the subject 101 and the grating (the first grating 21 and the third grating 23) adjacent to the second region 60b among the plurality of gratings in a case where the subject 101 is disposed in the second region 60b on the side of the detector 12 with respect to the first grating 21. With this configuration, in either the case where the subject 101 is disposed between the first grating 21 and the X-ray source 11, or the case where the subject 101 is disposed between the first grating 21 and the detector 12, the operator can confirm the disposition relationship between the subject 101 and the grating by visually confirming the captured images (the first captured image 2b and the second captured image 2c) captured by the first imaging unit 41 and the second imaging unit 42.

Further, in the present embodiment, as described above, the X-ray phase imaging system 100 includes the placement stage 31 disposed in the first region 60a or the second region 60b, on which the subject 101 is placed, and the operation unit 3 that receives the input operation to move the placement stage 31, and the first imaging unit 41 and the second imaging unit 42 (imaging unit) are configured to optically image the subject 101 in motion that is moving in the first region 60a on the basis of the input operation with respect to the operation unit 3, and to optically image the subject 101 in motion that is moving in the second region 60b on the basis of the input operation with respect to the operation unit 3. With this configuration, the subject 101 can be imaged while the subject 101 is moving on the basis of the input operation with respect to the operation unit 3, so that the operator can change the position of the subject 101 while confirming the captured image. Therefore, in a case where the position of the subject 101 is finely adjusted, it is possible to effectively restrain the subject 101 from coming into contact with the grating (the first grating 21 to the third grating 23).

Further, in the present embodiment, as described above, the X-ray phase imaging system 100 includes the placement stage 31 on which the subject 101 is placed, and the placement stage 31 is configured to rotate the subject 101 in a state in which the subject 101 is placed thereon, and the first imaging unit 41 and the second imaging unit 42 (imaging unit) optically image the subject 101 that is placed on the placement stage 31 and that is rotating and one or both of the first grating 21 and the second grating 22. With this configuration, the first imaging unit 41 and the second imaging unit 42 can image the subject 101 placed on the placement stage 31 and one or both of the first grating 21 and the second grating 22, so that the operator can determine whether or not the rotating subject 101 comes into contact with the first grating 21 and the second grating 22 by confirming the captured image (the first captured image 2*b* and the second captured image 2*c*). As a result, it is possible to restrain the rotating subject 101 from coming into contact with the grating.

The grating drive unit 21*b*, 22*b*, and 23*b* that perform at least one of moving and rotating the plurality of gratings (the first grating 21, the second grating 22, and the third grating 23) are provided, and the first imaging unit 41 and the second imaging unit 42 (imaging unit) optically image one or both of the first grating 21 and the second grating 22 which are performing at least one of movement and rotation. With this configuration, the first imaging unit 41 and the second imaging unit 42 can optically image the grating (one or both of the first grating 21 and the second grating 22) that performs at least one of movement and rotation, so that the operator can determine whether or not the subject 101 comes into contact with the first grating 21 and the second grating 22 by confirming the captured image (the first captured image 2*b* and the second captured image 2*c*). As a result, it is possible to restrain the subject 101 from coming into contact with the grating that performs at least one of movement and rotation.

Further, as described above, the X-ray phase imaging system 100 includes the first imaging unit 41 that optically images the subject 101 disposed in the first region 60*a* on the side of the X-ray source 11 with respect to the first grating 21 and the grating (the first grating 21 and the third grating 23) adjacent to the first region 60*a* among the plurality of gratings. Then, the X-ray phase imaging system 100 includes the second imaging unit 42 that is provided separately from the first imaging unit 41 and that optically images the subject 101 disposed in the second region 60*b* on the side of the detector 12 with respect to the first grating 21 and the grating (the first grating 21 and the second grating 22) adjacent to the second region 60*b* among the plurality of gratings. With this configuration, in a case where the subject 101 is disposed in the first region 60*a*, the subject 101 and the grating (the first grating 21 and the third grating 23) can be imaged by the first imaging unit 41. Further, in a case where the subject 101 is disposed in the second region 60*b*, the subject 101 and the grating (the first grating 21 and the second grating 22) can be imaged by the second imaging unit 42. As a result, in order to confirm that the subject 101 and the grating do not come into contact with each other, in either the case where the subject 101 is disposed between the first grating 21 and the X-ray source 11 or the case where the subject 101 is disposed between the first grating 21 and the detector 12, the disposition relationship between the subject 101 and the grating can be confirmed. Further, in a case where one imaging unit is configured to move beyond the first grating 21, it is considered that the apparatus configuration becomes complicated due to the provision of the movement mechanism for moving one imaging unit. On the other hand, in the present embodiment, since it is not necessary to provide the movement mechanism that causes complication, it is possible to restrain the apparatus configuration from being complicated. Further, the reason why the imaging unit is provided in each of the first region 60*a* and the second region 60*b* is that the present inventor has found that it is difficult to image both the first region 60*a* and the second region 60*b* with only one imaging unit disposed in either one of the first region 60*a* or the second region 60*b* due to the presence of the first grating 21 (that is, the first grating 21 optically partitions the first region 60*a* and the second region 60*b*).

Further, in the present embodiment, as described above, the first imaging unit 41 is disposed in the direction (Z1 direction side) perpendicular to the X-ray irradiation axis 10, in the first region 60*a*, and the second imaging unit 42 is disposed in the direction (Z1 direction side) perpendicular to the X-ray irradiation axis 10, in the second region 60*b*. With this configuration, both the first imaging unit 41 and the second imaging unit 42 can image all the gratings and the subject 101 while the subject 101 is placed on the placement stage 31. As a result, it is possible to more effectively confirm that the subject 101 does not come into contact with the grating, as compared with a case where the subject 101 is imaged from the direction (X direction) side parallel to the X-ray irradiation axis 10, that is, the side of the X-ray source 11 or the side of the detector 12 when viewed from the subject 101.

Further, in the present embodiment, as described above, the X-ray phase imaging system 100 includes the frame member 61 in which the grating holding unit 21*a*, the grating holding unit 22*a*, and the grating holding unit 23*a* that hold the plurality of gratings (the first grating 21, the second grating 22, and the third grating 23) from above are disposed, and the first imaging unit 41 and the second imaging unit 42 are disposed on the frame member 61. With this configuration, the first imaging unit 41 and the second imaging unit 42 are disposed on the frame member 61 instead of the wall surface (top surface) of the housing 60, so that the first imaging unit 41 and the second imaging unit 42 can be disposed above the subject 101 without providing a hole portion, such as a screw hole, in the housing 60. Therefore, the first imaging unit 41 and the second imaging unit 42 can be provided without drilling a hole in the housing 60 for shielding X-rays. As a result, it is possible to restrain the X-ray shielding rate from decreasing because the first imaging unit 41 and the second imaging unit 42 are provided.

Further, in the present embodiment, as described above, the X-ray phase imaging system 100 includes the control unit 1*a* (display control unit) that causes the display unit 2 (display device) to selectively display the first captured image 2*b* optically captured by the first imaging unit 41 and the second captured image 2*c* optically captured by the second imaging unit 42. With this configuration, the operator who captures the phase contrast image 2*a* can easily confirm the disposition of the subject 101 by visually confirming the first captured image 2*b* or the second captured image 2*c* displayed on the display unit 2.

Further, in the present embodiment, as described above, the X-ray phase imaging system 100 includes the placement stage 31 disposed in the first region 60*a* or the second region 60*b*, on which the subject 101 is placed, and the drive unit 32 (placement stage drive unit) that moves the placement stage 31 between the first region 60*a* and the second region 60*b*, and the control unit 1*a* (display control unit) is configured to display the first captured image 2*b* in a case where the placement stage 31 is disposed in the first region 60*a*, and to display the second captured image 2*c* in a case where the placement stage 31 is disposed in the second region 60*b*. With this configuration, the control unit 1*a* can automatically switch the display between the first captured image 2*b* and the second captured image 2*c*. As a result, in a case where the placement stage 31 on which the subject 101 is placed is moved beyond the first grating 21, the operator can easily confirm the image corresponding to the disposition of the placement stage 31. Further, the display is switched between the first captured image 2b and the second captured image 2c, so that it is possible to simplify the display screen as compared with a case where the first captured image 2b and the second captured image 2c are displayed side by side.

Further, in the present embodiment, as described above, the plurality of gratings include the third grating 23 disposed between the X-ray source 11 and the first grating 21, and the first imaging unit 41 and the second imaging unit 42 (imaging unit) are configured to optically image the subject 101 and the first grating 21 and the third grating 23 adjacent to the first region 60a in a case where the subject 101 is disposed in the first region 60a between the first grating 21 and the third grating 23, and to optically image the subject 101 and the first grating 21 and the second grating 22 adjacent to the second region 60b in a case where the subject 101 is disposed in the second region 60b between the first grating 21 and the second grating 22. With this configuration, the operator can confirm the first captured image 2b which is captured so as to include the first grating 21 and the third grating 23 that the subject 101 may come into contact with in the first region 60a in a case where the placement stage 31 is disposed in the first region 60a. Further, the operator can confirm the second captured image 2c which is captured so as to include the first grating 21 and the second grating 22 that the subject 101 may come into contact with in the second region 60b in a case where the placement stage 31 is disposed in the second region 60b. As a result, the operator can effectively restrain the subject 101 and the grating from coming into contact with each other by confirming the first captured image 2b and the second captured image 2c, regardless of whether the subject 101 is disposed in either the first region 60a or the second region 60b.

Further, in the present embodiment, as described above, the X-ray phase imaging system 100 includes the illumination unit 50 that irradiates the subject 101 with illumination light, and the first imaging unit 41 and the second imaging unit 42 (imaging unit) are configured to optically image the subject 101 while the subject 101 is irradiated with the illumination light from the illumination unit 50. With this configuration, in a case where the inside of the housing 60 in which the subject 101 is disposed is sealed, it is possible to image the subject 101 by using illumination light emitted from the illumination unit 50 as a light source. For example, the operator can image the subject 101 inside the housing 60 and confirm the disposition by using illumination light emitted from the illumination unit 50 as a light source, even in a case where the placement stage 31 is configured to move with the door portion of the housing 60 closed so that the operator does not come into contact with the placement stage 31 in motion. Further, in a case where the housing 60 in which the subject 101 is disposed is sealed in order to restrain the X-rays from leaking to the outside, the subject 101 on which the X-ray irradiation is being performed can be irradiated with illumination light by the illumination unit 50. Therefore, it is possible to confirm the subject 101 on which X-ray imaging is being performed.

Further, in the present embodiment, the first imaging unit 41 and the second imaging unit 42 (imaging unit) optically image the subject 101 and one or both of the first grating 21 and the second grating 22 to capture the first captured image 2b and the second captured image 2c (captured image) as moving images. With this configuration, it is possible to confirm the disposition relationship between the subject 101 and the grating in real time by confirming the first captured image 2b and the second captured image 2c as moving images. Therefore, it is possible to more reliably confirm that the subject 101 and the grating do not come into contact with each other.

Modification Example

It should be noted that the embodiment disclosed herein is an example in all respects and is not considered to be restrictive. The scope of the present invention is shown by the claims, not the description of the above-described embodiment, and includes all modifications (modification examples) within the meaning and scope equivalent to the claims.

For example, in the above embodiment, an example has been shown in which the X-ray phase imaging system 100 is configured to generate the phase contrast image 2a (CT image) by rotating the subject 101 placed on a placement stage 31, but the present invention is not limited thereto. In the present invention, the X-ray phase imaging system 100 may be configured to generate the phase contrast image 2a (fluoroscopic image) without rotating the subject 101. Alternatively, the subject 101 may be rotated not in the up-and-down direction (Z direction) but in the extending direction (X direction) of the X-ray irradiation axis 10, as the rotation axis. Alternatively, the X-ray imaging may be performed while rotating (moving) X-ray source 11 and the detector 12 without rotating the subject 101.

Further, in the above embodiment, an example has been shown in which the first imaging unit 41 and the second imaging unit 42 are disposed on the frame member 61 on the upper side (the Z1 direction side, the top surface side of the housing 60), but the present invention is not limited thereto. For example, the first imaging unit 41 and the second imaging unit 42 may be disposed directly inside the housing 60 on the upper wall surface (top surface). Alternatively, the first imaging unit 41 and the second imaging unit 42 may be disposed inside (first region 60a and second region 60b) the housing 60 not on the upper side but on the lateral side. Alternatively, the first imaging unit 41 may be disposed inside the housing 60 on the side of the X-ray source 11 (X2 direction side). Similarly, the second imaging unit 42 may be disposed inside the housing 60 on the side of the detector 12 (X1 direction side).

Figure 8:
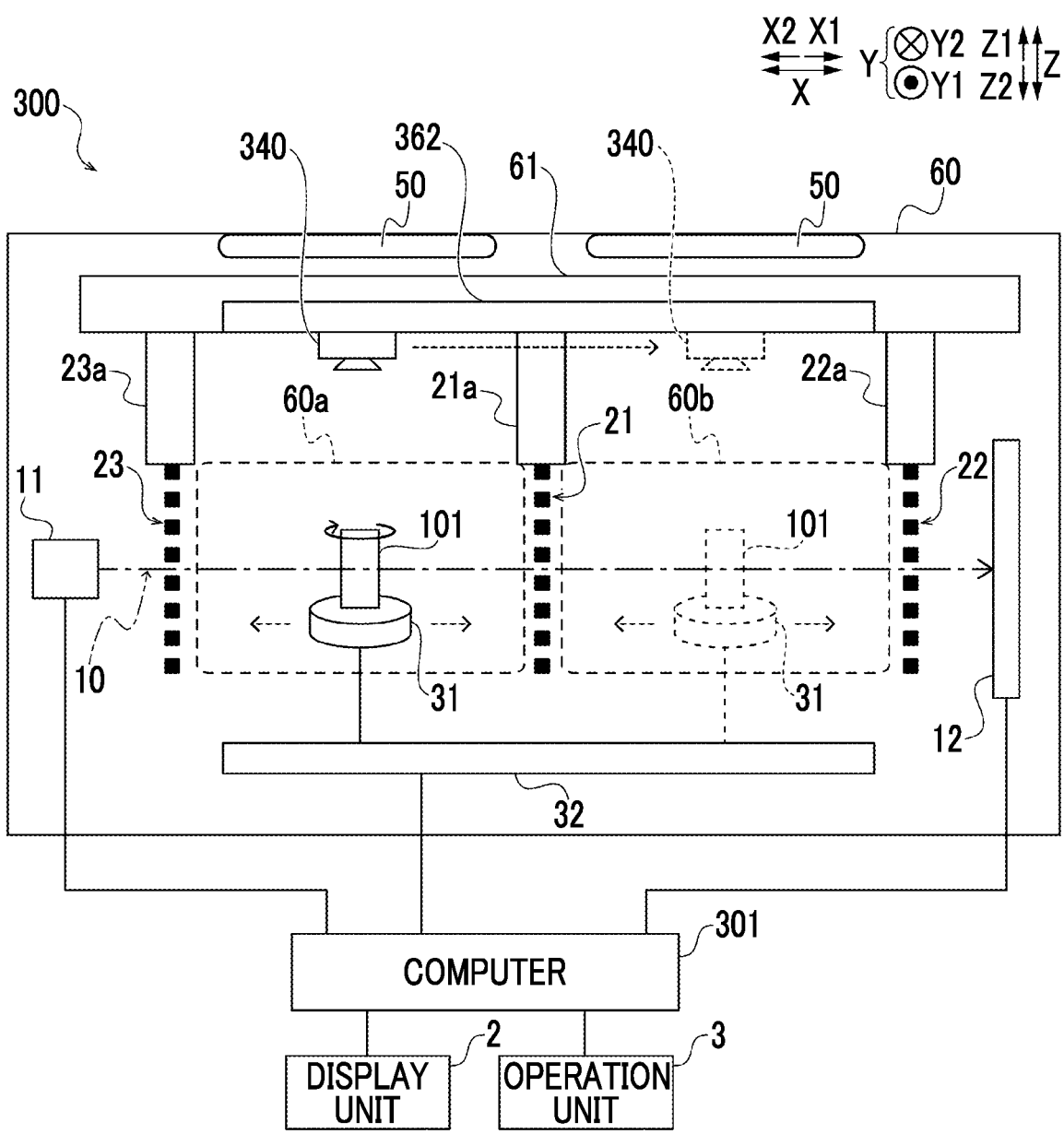
FIG. 8 is a schematic diagram showing a configuration of an X-ray phase imaging system according to a modification example of the present invention.

Further, in the above embodiment, an example has been shown in which two imaging units, that is, the first imaging unit 41 and the second imaging unit 42, are provided, but the present invention is not limited thereto. In the present invention, one imaging unit 340 may be provided as in an X-ray phase imaging system 300 according to a modification example shown in FIG. 8. In this case, the X-ray phase imaging system 300 includes an imaging unit drive unit 362 that moves the imaging unit 340. The imaging unit 340 is moved in the direction (X direction) along the X-ray irradiation axis 10 beyond the first grating 21 by the imaging unit drive unit 362, on the basis of the control signal from a computer 301. In this case, the imaging unit drive unit 362 moves the imaging unit 340 such that the imaging unit 340 is located above the first region 60a in a case where the placement stage 31 is located in the first region 60a, and moves the imaging unit 340 such that the imaging unit 340 is located above the second region 60b in a case where the placement stage 31 is located in the second region 60b. That is, the imaging unit 340 is configured to optically image the subject 101 placed on the placement stage 31 disposed in the first region 60a and the first grating 21 and the third grating 23, and to optically image the subject 101 placed on the placement stage 31 disposed in the second region 60b and the first grating 21 and the second grating 22, by being moved by the imaging unit drive unit 362.

With this, one imaging unit 340 is moved, so that it is possible to confirm the disposition relationship between the subject 101 and the plurality of gratings (the first grating 21, the second grating 22, and the third grating 23) on the basis of the captured image by one imaging unit 340, even in a case where the placement stage 31 is moved beyond the first grating 21. Further, since the imaging unit 340 can be moved according to the movement of the placement stage 31, the imaging unit 340 can be disposed directly above the placement stage 31 (Z1 direction side), even in a case where the placement stage 31 is moved along the X-ray irradiation axis 10 such that the enlargement ratio of the subject 101 in the captured image is finely adjusted within the first region 60a or within the second region 60b. Therefore, the subject 101 placed on the placement stage 31 can be imaged from directly above, so that it is possible to easily confirm the disposition relationship between the subject 101 and the grating (the first grating 21, the second grating 22, and the third grating 23).

Further, in the above embodiment, an example has been shown in which the X-ray source 11 and the detector 12 are disposed inside the housing 60 along the horizontal direction (right-and-left direction), but the present invention is not limited thereto. For example, a configuration may be adopted in which the X-ray source 11 and the detector 12 may be disposed along the vertical direction (up-and-down direction). In that case, it is preferable that the first imaging unit 41 and the second imaging unit 42 are disposed at positions (for example, the side wall portions) separated in the direction perpendicular to an X-ray irradiation axis from the position where the subject 101 is disposed.

Further, in the above embodiment, an example has been shown in which the illumination unit 50 is disposed on the wall surface of the housing 60, but the present invention is not limited thereto. For example, the illumination unit 50 may be disposed on the frame member 61 in the same manner as the first imaging unit 41 and the second imaging unit 42. Alternatively, the illumination units 50 may be disposed in the first imaging unit 41 and the second imaging unit 42, respectively.

Further, in the above embodiment, an example has been shown in which the placement stage 31 is moved between the first region 60a and the second region 60b by the drive unit 32, but the present invention is not limited thereto. For example, the placement stages 31 may be separately disposed in both the first region 60a and the second region 60b without providing the drive unit 32, respectively. In that case, the subject 101 is also selectively disposed in either the first region 60a or the second region 60b. Alternatively, the placement stage 31 is attachably and detchably formed and the placement stage 31 is attached to either the first region 60a or the second region 60b, whereby the placement stage 31 may be disposed in the first region 60a or the second region 60b.

Further, in the above embodiment, an example has been shown in which the display is switched between the first captured image 2b and the second captured image 2c on the basis of the movement of the placement stage 31, but the present invention is not limited thereto. For example, the display may be switched between the first captured image 2b and the second captured image 2c on the basis of the input operation with respect to the operation unit 3.

Further, in the above embodiment, an example has been shown in which the first imaging unit 41 images both the first grating 21 and the third grating 23, and the second imaging unit 42 images both the first grating 21 and the second grating 22, but the present invention is not limited thereto. For example, the first imaging unit 41 may have an angle of view capable of imaging only one of the first grating 21 and the third grating 23. Alternatively, the second imaging unit 42 may have an angle of view capable of imaging only one of the first grating 21 and the second grating 22.

Further, in the above embodiment, an example has been shown in which in the X-ray phase imaging system 100, the computer 1 (the control unit 1a and the image processing unit 1b), the display unit 2, and the operation unit 3 are disposed outside the housing 60, but the present invention is not limited thereto. For example, in the X-ray phase imaging system 100, the computer 1 (the control unit 1a and the image processing unit 1b), the display unit 2, and the operation unit 3 may be disposed at positions separated from the housing 60 in which the X-ray source 11 and the detector 12 are disposed. Alternatively, like a tablet PC, the display unit 2 and the operation unit 3 may be integrally formed in the computer 1.

Further, in the above embodiment, an example has been shown in which the control unit 1a and the image processing unit 1b are separately formed in the computer 1, but the present invention is not limited thereto. For example, the control unit 1a and the image processing unit 1b may constitute common hardware (processor).

Further, in the above embodiment, an example has been shown in which the subject 101 is directly placed on the placement stage 31, but the present invention is not limited thereto. For example, the subject 101 may be placed on the placement stage 31 in a state in which the subject 101 is attached to a subject holding unit that holds the subject 101.

Further, in the above embodiment, an example has been shown in which the display is switched to either the first captured image 2b or the second captured image 2c and the switched image is displayed on the display unit 2, but the present invention is not limited thereto. For example, the first captured image 2b and the second captured image 2c may be displayed side by side.

Further, in the above embodiment, an example of a configuration including three gratings, that is, the first grating 21, the second grating 22, and the third grating 23, as the plurality of gratings, has been shown, but the present invention is not limited thereto. For example, the plurality of gratings may not include the third grating 23. In a case where the plurality of gratings do not include the third grating 23, the X-ray phase imaging system 100 need only include an X-ray source 11 capable of emitting X-rays having high coherence. Further, in that case, the first imaging unit 41 may be configured to have an angle of view capable of imaging the X-ray source 11 (cover member of the X-ray source 11) and the first grating 21.

Aspect

It will be appreciated by a person skilled in the art that the above-described exemplary embodiments are specific examples of the following aspects.

Item 1

An X-ray phase imaging system including:
an X-ray source that irradiates a subject with X-rays;

a detector that detects the X-rays emitted from the X-ray source;
a plurality of gratings that are disposed between the X-ray source and the detector, and that include a first grating which is irradiated with the X-rays from the X-ray source and a second grating which is irradiated with X-rays from the first grating; and
an imaging unit that optically images the subject and one or both of the first grating and the second grating.

Item 2

The X-ray phase imaging system according to Item 1,
in which the imaging unit
optically images, in a case where the subject is disposed in a first region on a side of the X-ray source with respect to the first grating, the subject and a grating adjacent to the first region among the plurality of gratings, and optically images, in a case where the subject is disposed in a second region on a side of the detector with respect to the first grating, the subject and a grating adjacent to the second region among the plurality of gratings.

Item 3

The X-ray phase imaging system according to Item 2, further including:
a placement stage on which the subject is placed, the placement stage being disposed in the first region or the second region; and
an operation unit that receives an input operation to move the placement stage,
in which the imaging unit is configured to optically image the subject in motion that is moving in the first region, on the basis of the input operation with respect to the operation unit, and to optically image the subject in motion that is moving in the second region, on the basis of the input operation with respect to the operation unit.

Item 4

The X-ray phase imaging system according to any one of Items 1 to 3, further including:
a placement stage on which the subject is placed,
in which the placement stage is configured to rotate the subject in a state in which the subject is placed on the placement stage, and
the imaging unit optically images the subject that is placed on the placement stage and that is rotating and one or both of the first grating and the second grating.

Item 5

The X-ray phase imaging system according to any one of Items 1 to 4, further including:
a grating drive unit that performs at least one of moving and rotating the plurality of gratings,
in which the imaging unit optically images one or both of the first grating and the second grating which are performing at least one of movement and rotation.

Item 6

The X-ray phase imaging system according to any one of Items 1 to 5,
in which the imaging unit includes
a first imaging unit that optically images the subject disposed in a first region on a side of the X-ray source with respect to the first grating and a grating adjacent to the first region among the plurality of gratings, and
a second imaging unit that is provided separately from the first imaging unit and that optically images the subject disposed in a second region on a side of the detector with respect to the first grating and a grating adjacent to the second region among the plurality of gratings.

Item 7

The X-ray phase imaging system according to Item 6,
in which the first imaging unit is disposed in a direction perpendicular to an X-ray irradiation axis, in the first region, and
the second imaging unit is disposed in a direction perpendicular to the X-ray irradiation axis, in the second region.

Item 8

The X-ray phase imaging system according to Item 7, further including:
a frame member in which a grating holding unit that holds the plurality of gratings from above is disposed,
in which the first imaging unit and the second imaging unit are disposed on the frame member.

Item 9

The X-ray phase imaging system according to any one of Items 6 to 8, further including:
a display control unit that causes a display device to selectively display a first captured image optically captured by the first imaging unit and a second captured image optically captured by the second imaging unit.

Item 10

The X-ray phase imaging system according to Item 9, further including:
a placement stage on which the subject is placed, the placement stage being disposed in the first region or the second region; and
a placement stage drive unit that moves the placement stage between the first region and the second region,
in which the display control unit is configured to display the first captured image in a case where the placement stage is disposed in the first region, and to display the second captured image in a case where the placement stage is disposed in the second region.

Item 11

The X-ray phase imaging system according to any one of Items 1 to 10:
in which the plurality of gratings further include a third grating disposed between the X-ray source and the first grating, and
the imaging unit is configured to
optically image, in a case where the subject is disposed in a first region provided between the first grating and the third grating, the first grating and the third grating, which are adjacent to the first region, and the subject, and optically image, in a case where the subject is disposed in a second region provided between the first grating and the second grating, the first grating and the second grating, which are adjacent to the second region, and the subject.

Item 12

The X-ray phase imaging system according to any one of Items 1 to 11, further including:
an illumination unit that irradiates the subject with illumination light,
in which the imaging unit is configured to optically image the subject while the subject is irradiated with the illumination light from the illumination unit.

Item 13

The X-ray phase imaging system according to any one of Items 1 to 5,
in which one imaging unit is provided, and
the X-ray phase imaging system further comprises an imaging unit drive unit that moves the imaging unit.

Item 14

The X-ray phase imaging system according to any one of Items 1 to 13,
wherein the imaging unit optically images the subject and one or both of the first grating and the second grating to capture a captured image as a moving image.

What is claimed is:

1. An X-ray phase imaging system comprising:
an X-ray source that irradiates a subject with X-rays;
a detector that detects the X-rays emitted from the X-ray source;
a plurality of gratings that are disposed between the X-ray source and the detector, and that include a first grating which is irradiated with the X-rays from the X-ray source and a second grating which is irradiated with X-rays from the first grating; and
an imaging unit that optically images the subject and one or both of the first grating and the second grating.

2. The X-ray phase imaging system according to claim 1, wherein the imaging unit
optically images, in a case where the subject is disposed in a first region on a side of the X-ray source with respect to the first grating, the subject and a grating adjacent to the first region among the plurality of gratings, and
optically images, in a case where the subject is disposed in a second region on a side of the detector with respect to the first grating, the subject and a grating adjacent to the second region among the plurality of gratings.

3. The X-ray phase imaging system according to claim 2, further comprising:
a placement stage on which the subject is placed, the placement stage being disposed in the first region or the second region; and
an operation unit that receives an input operation to move the placement stage,
wherein the imaging unit is configured to optically image the subject in motion that is moving in the first region, on the basis of the input operation with respect to the operation unit, and to optically image the subject in motion that is moving in the second region, on the basis of the input operation with respect to the operation unit.

4. The X-ray phase imaging system according to claim 1, further comprising:
a placement stage on which the subject is placed,
wherein the placement stage is configured to rotate the subject in a state in which the subject is placed on the placement stage, and
the imaging unit optically images the subject that is placed on the placement stage and that is rotating and one or both of the first grating and the second grating.

5. The X-ray phase imaging system according to claim 1, further comprising:
a grating drive unit that performs at least one of moving and rotating the plurality of gratings,
wherein the imaging unit optically images one or both of the first grating and the second grating which are performing at least one of movement and rotation.

6. The X-ray phase imaging system according to claim 1, wherein the imaging unit includes
a first imaging unit that optically images the subject disposed in a first region on a side of the X-ray source with respect to the first grating and a grating adjacent to the first region among the plurality of gratings, and
a second imaging unit that is provided separately from the first imaging unit and that optically images the subject disposed in a second region on a side of the detector with respect to the first grating and a grating adjacent to the second region among the plurality of gratings.

7. The X-ray phase imaging system according to claim 6, wherein the first imaging unit is disposed in a direction perpendicular to an X-ray irradiation axis, in the first region, and
the second imaging unit is disposed in a direction perpendicular to the X-ray irradiation axis, in the second region.

8. The X-ray phase imaging system according to claim 7, further comprising:
a frame member in which a grating holding unit that holds the plurality of gratings from above is disposed,
wherein the first imaging unit and the second imaging unit are disposed on the frame member.

9. The X-ray phase imaging system according to claim 6, further comprising:
a display control unit that causes a display device to selectively display a first captured image optically captured by the first imaging unit and a second captured image optically captured by the second imaging unit.

10. The X-ray phase imaging system according to claim 9, further comprising:
a placement stage on which the subject is placed, the placement stage being disposed in the first region or the second region; and
a placement stage drive unit that moves the placement stage between the first region and the second region,
wherein the display control unit is configured to display the first captured image in a case where the placement stage is disposed in the first region, and to display the second captured image in a case where the placement stage is disposed in the second region.

11. The X-ray phase imaging system according to claim 1,
wherein the plurality of gratings further include a third grating disposed between the X-ray source and the first grating, and the imaging unit is configured to
optically image, in a case where the subject is disposed in a first region provided between the first grating and the third grating, the first grating and the third grating, which are adjacent to the first region, and the subject, and optically image, in a case where the subject is disposed in a second region provided between the first grating and the second grating, the first grating and the second grating, which are adjacent to the second region, and the subject.

12. The X-ray phase imaging system according to claim 1, further comprising:

an illumination unit that irradiates the subject with illumination light, wherein the imaging unit is configured to optically image the subject while the subject is irradiated with the illumination light from the illumination unit.

13. The X-ray phase imaging system according to claim 1, wherein one imaging unit is provided, and
the X-ray phase imaging system further comprises an imaging unit drive unit that moves the imaging unit.

14. The X-ray phase imaging system according to claim 1, wherein the imaging unit optically images the subject and one or both of the first grating and the second grating to capture a captured image as a moving image.

\* \* \* \* \*